(12) United States Patent
Adachi et al.

(10) Patent No.: US 9,575,082 B2
(45) Date of Patent: Feb. 21, 2017

(54) AUTOMATIC ANALYSIS DEVICE AND AUTOMATIC ANALYSIS METHOD

(71) Applicant: HITACHI HIGH-TECHNOLOGIES CORPORATION, Tokyo (JP)

(72) Inventors: Sakuichiro Adachi, Tokyo (JP); Hajime Yamazaki, Tokyo (JP); Masahiko Iijima, Tokyo (JP); Shigeki Matsubara, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/786,234

(22) PCT Filed: Jun. 5, 2014

(86) PCT No.: PCT/JP2014/064971
§ 371 (c)(1),
(2) Date: Oct. 22, 2015

(87) PCT Pub. No.: WO2014/203741
PCT Pub. Date: Dec. 24, 2014

(65) Prior Publication Data
US 2016/0077119 A1    Mar. 17, 2016

(30) Foreign Application Priority Data
Jun. 19, 2013    (JP) ................. 2013-128608

(51) Int. Cl.
*G01N 21/00*    (2006.01)
*G01N 15/06*    (2006.01)
(Continued)

(52) U.S. Cl.
CPC ........ *G01N 35/00584* (2013.01); *G01N 21/82* (2013.01); *G01N 21/51* (2013.01);
(Continued)

(58) Field of Classification Search
CPC ........ G01N 21/00; G01N 15/06; G01N 33/00; G01N 33/48
(Continued)

(56) References Cited

U.S. PATENT DOCUMENTS 5,506,679 A * 4/1996 Cooper et al. ................. 356/338
6,323,949 B1 * 11/2001 Lading et al. ................. 356/477
(Continued)

FOREIGN PATENT DOCUMENTS

JP    5-79984 A    3/1993
JP    6-303992 A    11/1994
(Continued)

OTHER PUBLICATIONS

International Search Report of PCT/JP2014/064971.

*Primary Examiner* — Brian J Sines
(74) *Attorney, Agent, or Firm* — Mattingly & Malur, PC

(57) ABSTRACT

The automatic analysis device includes an analysis unit that corrects, based on a measured value at the time of a first light amount measurement with water dispensed in the reaction cell before the sample is dispensed therein; a measured value at the time of a second light amount measurement after the sample and a preprocessing reagent are dispensed into the reaction cell; a liquid amount in the reaction cell at the time of the second light amount measurement; and a liquid amount in the reaction cell at the time of a third light amount measurement after the reaction reagent has been dispensed into the reaction cell and before the reaction reagent and the substance to be measured react with each other.

6 Claims, 10 Drawing Sheets

(51) Int. Cl.
  *G01N 33/00*   (2006.01)
  *G01N 33/48*   (2006.01)
  *G01N 35/00*   (2006.01)
  *G01N 21/82*   (2006.01)
  *G01N 21/51*   (2006.01)
  *G01N 21/59*   (2006.01)

(52) U.S. Cl.
  CPC ............ *G01N 21/59* (2013.01); *G01N 35/00* (2013.01); *G01N 2021/825* (2013.01); *G01N 2035/00891* (2013.01)

(58) Field of Classification Search
  USPC ............ 422/50, 68.1, 400, 402, 403, 82.09, 73,422/81, 82.05, 63, 64, 65, 66; 436/43, 164, 165, 436/171; 356/338, 441, 477; 702/189
  See application file for complete search history.

(56) References Cited

U.S. PATENT DOCUMENTS

| | | | |
|---|---|---|---|
| 2003/0128363 A1* | 7/2003 | Aberle et al. | 356/441 |
| 2004/0016686 A1* | 1/2004 | Wyatt | 210/94 |
| 2008/0306713 A1* | 12/2008 | Suzuki | 702/189 |
| 2013/0108509 A1 | 5/2013 | Shiba et al. | |
| 2013/0301048 A1 | 11/2013 | Makino et al. | |

FOREIGN PATENT DOCUMENTS

| | | |
|---|---|---|
| JP | 2876253 B2 | 3/1999 |
| JP | 2013-068443 A | 4/2013 |
| WO | 2011/162113 A1 | 12/2011 |
| WO | 2012/098946 A1 | 7/2012 |

* cited by examiner

Concentration series of disturbance substance

FIG. 15

```
                    ,1502                   ,1503
           Specimen number  [1001]   Specimen position  [ 1 ]

Quantitation   ,1504
           result
```

| Examination item | Quantitation result | Quantitation result after correction |
|---|---|---|
| PG I | (20°) 63.3 ng / mL ( ! ) | 67 ng / mL (Sample influence large) |

AUTOMATIC ANALYSIS DEVICE AND AUTOMATIC ANALYSIS METHOD

TECHNICAL FIELD

The present invention relates to an automatic analysis device for automatically measuring the concentration of substance included in a sample, and an analysis method therefor.

BACKGROUND ART

Automatic analysis devices are being widely utilized that calculate, according to the Lambert-Beer law, absorbance from the amount of transmitted light obtained when a reaction solution having a sample and a reagent mixed therein is irradiated with light, and that then quantitate the concentration of a component in the sample on the basis of the amount of change in the absorbance within a certain time. In such devices, a number of reaction cells holding the reaction solution are arranged along the circumference direction of a reaction disc that is rotatably driven. Around the reaction disc, an absorbance measuring unit is disposed, and the absorbance measuring unit measures the absorbance of the reaction solution at the intervals of approximately once every 15 seconds for about 10 minutes. The measured time-series data are referred to as reaction process data, and the component in the sample is quantitated from the amount of change in a certain time.

The reaction measured by the automatic analysis device includes the two types of a color reaction using a substrate and an enzyme, and an immune agglutination reaction using an antigen and an antibody. The method of quantitating concentration by the color reaction is referred to as biochemical analysis, where the examination items may include LDH (lactic acid dehydrogenase), ALP (alkaline phosphatase), and AST (aspartate-oxoglutarate aminotransferase), for example. The method of determining substance concentration by the immune agglutination reaction is referred to as immunoassay, where the examination items may include CRP (C-reactive protein), IgG (immunoglobulin), and RF (rheumatoid factor), for example. The examination items measured by the immune agglutination reaction may include those that have a relatively low blood concentration of the component and that therefore require high-sensitivity detection. In such a case, a latex reagent in which latex particles are bonded to the antibody as a sensitizer is often used. Such immune agglutination reaction is referred to as a latex immune agglutination reaction. In the latex immune agglutination reaction, the latex particles aggregate via the component, forming an aggregate. The higher the component concentration, the greater the size of the aggregate will be after a certain time. Thus, during sample measurement, the reaction solution is irradiated with light, and the amount of change in light amount or the amount of change in absorbance in a certain time is measured. Then, the measured value is compared with a calibration measurement result of measuring a calibrator with a known concentration so as to determine the component concentration. In order to further increase the sensitivity of such latex immune agglutination reaction, a method of measuring scattered light has been attempted. For example, a system and the like have been proposed whereby transmitted light and scattered light are separated using a diaphragm, and absorbance and the scattered light are simultaneously measured.

CITATION LIST

Patent Literature

Patent Literature 1: JP 2876253 B

SUMMARY OF INVENTION

Technical Problem

The scattered light measurement enables enhanced detection of a light amount change due to reaction compared with the transmitted light measurement. However, in the scattered light measurement, if there is disturbance substance other than the substance to be measured on the optical path (such as in a reaction cell or a reaction solution therein) prior to entry of the light into the light receiving unit, the measurement result is readily subject to optical influences. The substance to be measured may include latex particles or an aggregate of the latex particles. The disturbance substance may include scratches or contamination on the reaction cell, or fat globules or fibrin clot included in the sample.

In the case of absorbance measurement, the absorbance due to disturbance substance included in the reaction cell and the sample does not change basically. Accordingly, during absorbance measurement, by subtracting the influence of the disturbance substance from the overall measured value, the influence of the disturbance substance can be corrected for. However, in the case of scattered light measurement, there has not been any specific method for correcting for the influence of disturbance substance, so that the influence of disturbance substance could not be corrected. Thus, it has been necessary to use a reaction cell having little contamination or scratches so that their influence can be disregarded. In the case of a sample including a large amount of disturbance substance, it has been necessary to dilute the sample before measurement so that the influence of the disturbance substance can be disregarded. Such techniques, however, require much time and effort and are bothersome.

For example, in a particle diameter distribution measuring device according to Patent Literature 1, a data processing method relating to scattered light measurement is adopted. However, the processing method described in Patent Literature 1 is a data processing method for determining an accurate particle diameter even when the substance to be measured has a high concentration, and no data processing method is disclosed whereby the amount of scattered light from the substance to be measured can be accurately determined even when the reaction cell is contaminated or when there is disturbance substance in the sample other than the substance to be measured.

Solution to Problem

In order to solve the problem, an automatic analysis device according to the present invention includes an analysis unit that corrects, based on a measured value at the time of a first light amount measurement with water dispensed in the reaction cell before the sample is dispensed therein; a measured value at the time of a second light amount measurement after the sample and a preprocessing reagent have been dispensed into the reaction cell; a liquid amount in the reaction cell at the time of the second light amount measurement; and a liquid amount in the reaction cell at the time of a third light amount measurement after the reaction reagent has been dispensed into the reaction cell and before the reaction reagent and the substance to be measured react with each other, the amount of scattered light at the time of the third light amount measurement and the amount of scattered light at the time of a fourth light amount measurement after the reaction reagent and the substance to be measured have reacted, and then computes the concentration of the substance to be measured based on an after-correction value.

Advantageous Effects of Invention

According to the present invention, during measurement of the concentration of a substance to be measured in a sample by scattered light measurement, even when the influence of disturbance substance is expected, a quantitation result free of the influence of disturbance substance can be obtained. The other problems, configurations, and effects will become apparent from the following description of embodiments.

BRIEF DESCRIPTION OF DRAWINGS

FIG. 15 is a diagram of an example of a measurement result display screen according to the example.

DESCRIPTION OF EMBODIMENTS

In the following, embodiments of the present invention will be described with reference to the drawings. The embodiments of the present invention are not limited to an example which will be described below, and various modifications may be made within the technical concept of the present invention.

[Concept of Data Processing]

In the following, the basic concept of a data processing function will be described, the function enabling highly accurate computation of the concentration of a substance to be measured even in the presence of a plurality of disturbance substances (or disturbance factors, in the sense including scratches on the reaction cell). In the following description, a biochemical automatic analysis device equipped with the data processing function will be simply referred to as an "automatic analysis device".

Figure 1:
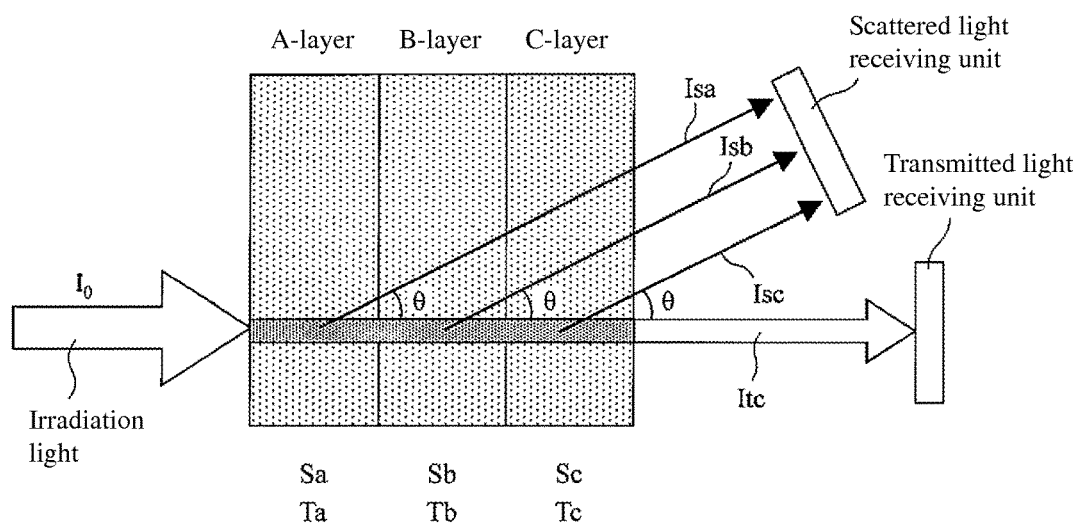
FIG. 1 is a diagram of a model in the presence of a plurality of disturbance substances.

Herein, a state in the presence of a plurality of disturbance substances will be described with reference to a model in which a plurality of scattering bodies are disposed in layers. FIG. 1 illustrates the model, in which three kinds of scattering bodies are substituted by a multilayer scattering body configured from an A-layer, a B-layer, and a C-layer.

The model considered herein is such that the multilayer scattering body of FIG. 1 is irradiated with an amount $I0$ of light, wherein a light receiving unit (hereafter referred to as a "scattered light receiving unit") receives scattered light output in a direction of an angle θ (≠0) with respect to the straight direction of travel of the light. Herein, the amount of light finally received by the scattered light receiving unit is Isall; Ta, Tb, and Tc are the transmittance of the respective layers when present by themselves; and Sa, Sb, and Sc are the ratios (scattering efficiency) of the amount of scattered light received by the scattered light receiving unit to the amount of irradiation light. Strictly speaking, the layers may have different angles to the light receiving unit; however, for the sake of simplifying description, it is assumed herein that the layers have no difference in angle. It is also assumed that multiple scattering of twice or more leads to a decrease in the amount of light and can therefore be disregarded. While the transmittance of each layer in the θ-direction may possibly be different from the transmittance in the straight direction of travel due to different optical path lengths depending on the angle, such transmittance is not considered herein for sake of simplifying description.

The amount of scattered light produced in the A-layer can be expressed as the value of the amount of irradiation light multiplied by the scattering efficiency, namely $I0 \times Sa$. The scattered light produced in the A-layer is attenuated in the B-layer and the C-layer before reaching the scattered light receiving unit. Accordingly, the amount of scattered light Isa from the A-layer that is finally received by the scattered light receiving unit can be approximately calculated to be $I0 \times Sa \times Tb \times Tc$. The amount Ita of transmitted light that passes through the A-layer and enters the B-layer can be calculated as $I0 \times Ta$.

The amount Isb of scattered light produced in the B-layer can be approximately calculated to be the value of the amount of transmitted light Ita multiplied by the scattering efficiency, namely $I0 \times Ta \times Sb$. The scattered light produced in the B-layer is attenuated in the C-layer before reaching the scattered light receiving unit. Accordingly, the amount of scattered light Isb from the B-layer that is finally received by the scattered light receiving unit can be approximately calculated to be $I0 \times Ta \times Sb \times Tc$. The amount of transmitted light Itb that passes through the B-layer and enters the C-layer can be calculated as $I0 \times Ta \times Tb$.

The amount of scattered light Isc produced in the C-layer can be expressed as the value of the amount of transmitted light Itb multiplied by the scattering efficiency, namely I0×Ta×Tb×Sc. The scattered light produced in the C-layer is received by the scattered light receiving unit without being attenuated.

The amount of transmitted light Itc that has passed through all of the A-layer, the B-layer, and the C-layer can be calculated as I0×Ta×Tb×Tc, which is received by the transmitted light receiving unit.

The light amount Isall that is finally received by the scattered light receiving unit is a total of the amounts of scattered light produced from the A-layer, the B-layer, and the C-layer, and can be therefore expressed as follows:

$$Isall = Isa + Isb + Isc \quad\quad \text{[Expression 1]}$$
$$= I0 \times (Sa \times Tb \times Tc + Ta \times Sb \times Tc + Ta \times Tb \times Sc)$$

Thus, the amount of the entire scattered light produced from the A-layer, the B-layer, and the C-layer can be approximately calculated by a computing method whereby the scattered light produced from each of the A-layer, the B-layer, and the C-layer is attenuated by another layer, even when the sequence of irradiation of the layers with the irradiating light is varied.

The above-described model is applied to the substance to be measured and the disturbance substance in the automatic analysis device, where the A-layer corresponds to reaction cell contamination (disturbance substance), the B-layer corresponds to fat globule in the sample (disturbance substance), and the C-layer corresponds to aggregating latex reagent (the substance to be measured).

In normal state, the reaction cell is free of contamination or scratches, and the sample does not include any disturbance substance. Accordingly, in normal state, the transmittance Ta and Tb can be considered to be "1", and the scattering efficiency Sa and Sb can be considered to be "0".

On the other hand, if the reaction cell has contamination and/or if the sample is in chylous state, indicating the presence of disturbance substance, the transmittance Ta and Tb will be equal to or less than "1", and the scattering efficiency Sa and Sb will have values greater than "0".

According to the data processing proposed in the present Description, the amount of scattered light from each disturbance substance and the transmittance thereof are approximately calculated from measured values obtained during a reaction process, and the true amount of scattered light of the substance to be measured is calculated from the measurement results of a number of scattering bodies as a whole. Of the values optically measured during the reaction process, the amount of scattered light can be computed by multiplying the amount of irradiation light with the scattering efficiency, while the transmittance can be computed according to the ratio of the amount of transmitted light.

Figure 2:
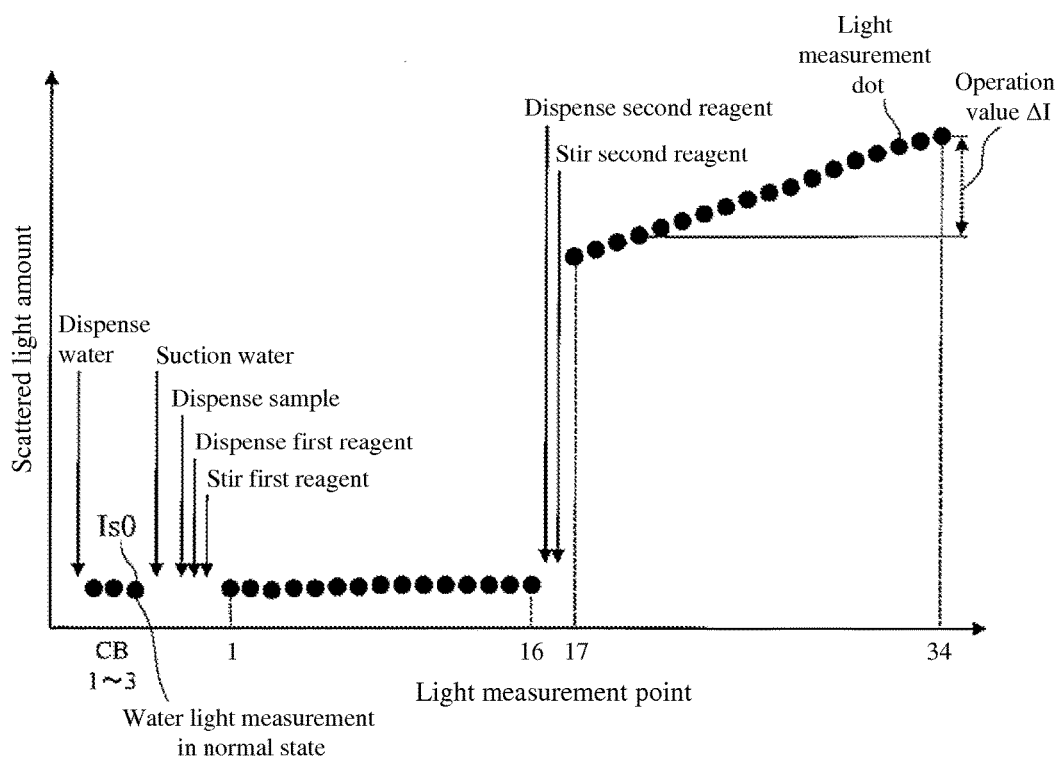
FIG. 2 is a diagram of a reaction process for scattered light measurement in normal state.
Figure 3:
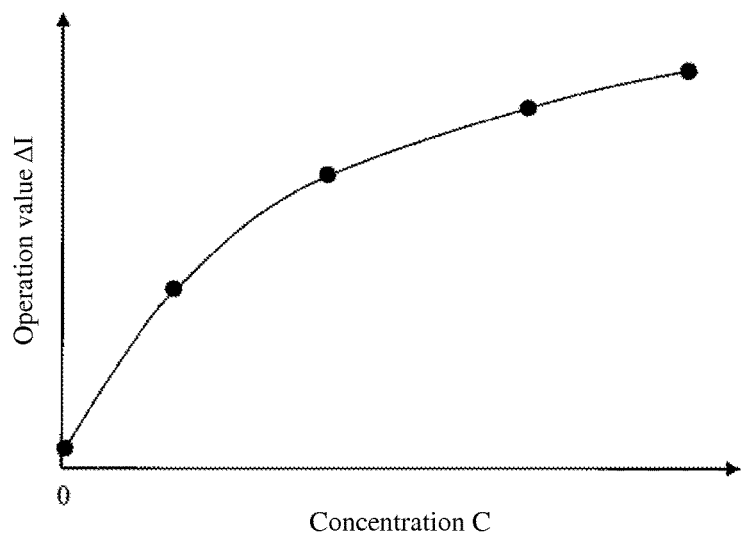
FIG. 3 is a diagram of a calibration curve representing the relationship of operation value and concentration.

FIG. 2 illustrates an example of the reaction process for scattered light measurement at a certain concentration during calibration measurement in a case where the scattered light receiving unit capable of measuring scattered light is disposed on the automatic analysis device. FIG. 3 shows a calibration curve for a latex agglutination reaction.

As illustrated in FIG. 2, first, water is dispensed into the reaction cell, and the amount of scattered light is measured three times (hereafter referred to as "water blank measurement"; CB1-3). Then, the water is suctioned from the reaction cell and, after the sample (S) and a first reagent (R1) are dispensed into the reaction cell and stirred, the amount of scattered light is measured 16 times (from the first point to the 16th point). Then, a latex reagent as a second reagent (R2) is dispensed into the reaction cell and stirred, and the amount of scattered light is measured 18 times (from the 17th point to the 34th point). After the second reagent is discharged, the latex particles, i.e., the substance to be measured, agglutinate in accordance with the concentration of a component included in the sample, whereby the amount of scattered light increases. The automatic analysis device calculates a difference between the amount of light prior to the agglutination reaction and the amount of light after the agglutination reaction following the dispensing of the latex reagent as an operation value ΔI, and creates a calibration curve indicating the relationship between the concentration and the operation value ΔI (FIG. 3).

At the time of the calibration curve measurement, the reaction cell has so little contamination or scratches so that their influence can be disregarded, and a calibrator having virtually no disturbance substance that would have an optical influence, such as fat globules, are used. Thus, the disturbance substance in the reaction cell and the sample can be disregarded, whereby the transmittance can be considered to be "1" and the scattering efficiency to be "0".

For reasons of data processing computation by the automatic analysis device, the third water blank measurement is considered the water light amount measurement in normal state, where the amount of scattered light is Is0, and the amount of transmitted light is It0.

Figure 4:
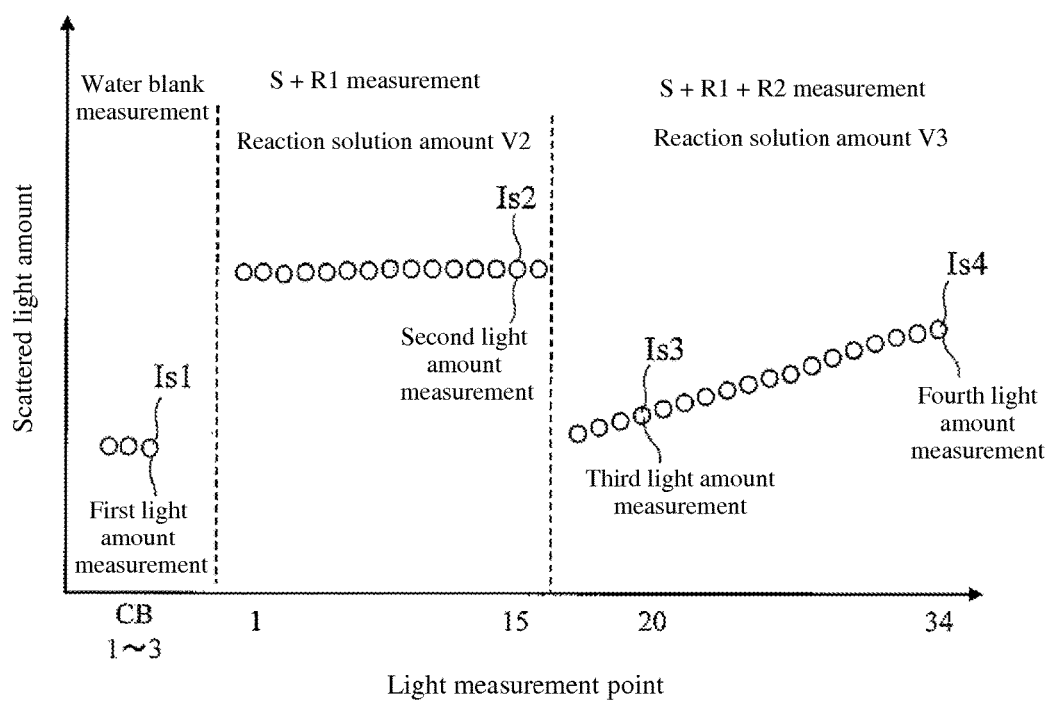
FIG. 4 is a diagram of a reaction process for scattered light measurement in the presence of disturbance substance.
Figure 5:
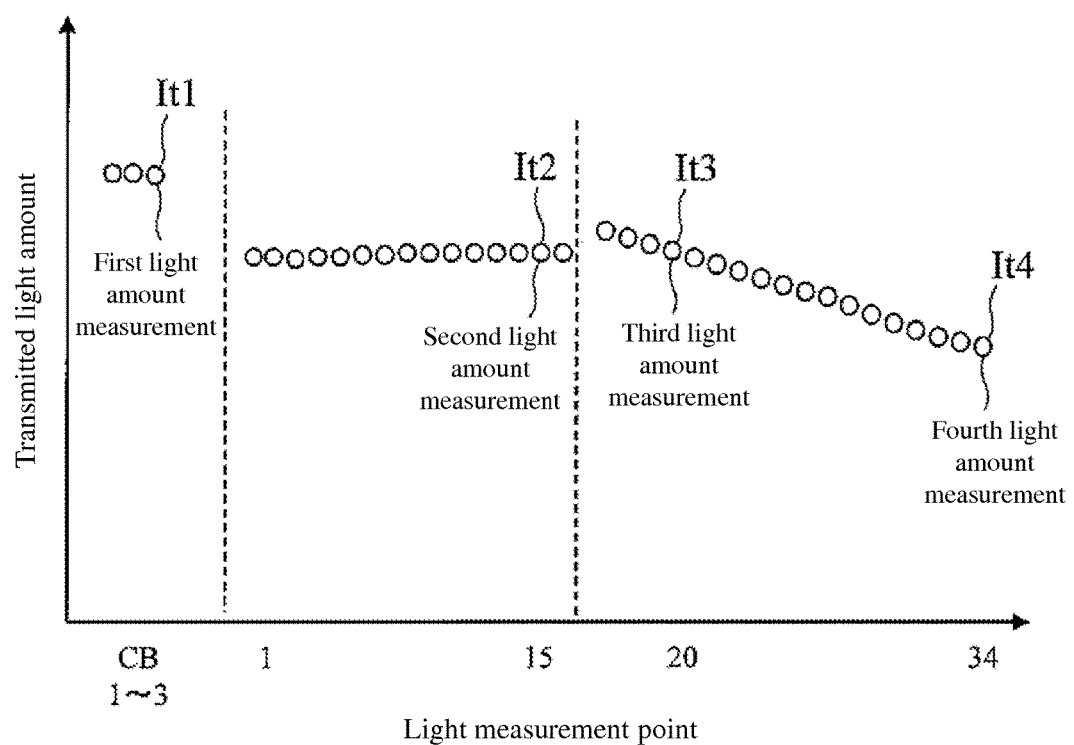
FIG. 5 is a diagram of a reaction process for transmitted light measurement in the presence of disturbance substance.

FIG. 4 and FIG. 5 illustrate reaction process data of scattered light measurement and transmitted light measurement during sample measurement where disturbance substance is included in the reaction cell and the sample. The steps of dispensing and stirring are the same as those for the calibration measurement illustrated in FIG. 2.

In the case of FIG. 4 and FIG. 5, the irradiation light is scattered by the disturbance substance, so that the amounts of scattered light at the time of the water blank measurement and at the time of the S+R1 measurement have greater values than during the calibration measurement including no disturbance substance.

For reasons of data processing computation in the automatic analysis device, the third water blank measurement is considered the first light amount measurement, where the amount of scattered light is Is1, and the amount of transmitted light is It1. The 15th point of the S+R1 measurement is considered the second light amount measurement, where the amount of scattered light is Is2, and the amount of transmitted light is It2. The 20th point of the S+R1+R2 measurement is considered the third light amount measurement, where the amount of scattered light is Is3, and the amount of transmitted light is It3. The 34th point of the S+R1+R2 measurement is considered the fourth light amount measurement, where the amount of scattered light is Is4, and the amount of transmitted light is It4.

Herein, from the light measurement values at the time of the first light amount measurement, the transmittance and the amount of scattered light of the reaction cell can be approximately calculated. From the light measurement values at the time of the second light amount measurement, by removing the influence of the reaction cell that has already been approximately calculated, the transmittance and the amount of scattered light of the disturbance substance in the sample can be approximately calculated. From the light measurement values at the time of the third and the fourth light amount measurements, by removing the influence of disturbance substance in the reaction cell and the sample that has already been approximately calculated, the light measurement values from the object of measurement without the influence of disturbance substance can be approximately calculated.

In the following, the content of data processing executed by the automatic analysis device when approximately calculating the above-described values from the light measurement values will be described.

First, the content of data processing executed when the transmittance and the amount of scattered light of the reaction cell are approximately calculated will be described. When the amount of scattered light due to the influence of a disturbance factor (such as scratches or contamination) present in the reaction cell is Scell, Scell is given by the difference between the light measurement value Is1 at the time of the first light amount measurement during sample measurement and the light measurement value Is0 at the time of the water light amount measurement during calibration measurement as follows.

$$Scell = Is1 - Is0 \quad \text{[Expression 2]}$$

wherein Is0 may be "0". Because Is0 indicates the water measurement light amount in normal state having no disturbance substance, an average value of the water blank measurements for all of a number of reaction cells that exist in the automatic analysis device may be used. Further, Is0 may be determined to be a certain value selected from the past measurement data. Thus, when an alternative value is used as Is0, the accuracy of the computed amount of scattered light Scell decreases. However, when the alternative value is used, the value of Is0 can be specified without depending on a single calibration measurement result, whereby the stability of Is0 can be increased. As a result, the accuracy of the finally approximately calculated amount Scell of the scattered light can be increased.

Next, when the transmittance of the reaction cell is Tcell, Tcell is given as follows.

$$Tcell = It1/It0 \quad \text{[Expression 3]}$$

While the Tcell may be considered the influence of light attenuation in the reaction cell, the optical path traveled by the scattered light is longer than the optical path of the straight-travelling transmitted light by $1/\tan\theta$ because accurately, the scattered light in the $\theta$-direction is measured. Thus, accurately, it is better to approximately calculate and use the transmittance Tcell (A) in the $\theta$-direction. However, in order to simplify description, the optical path length herein is considered the same as the straight direction of travel. The transmittance may be calculated from the absorbance Acell of the reaction cell (the absorbance when the optical path length is L') that is determined by a separately prepared absorptiometer and the like. In that case, Acell will be expressed by $$Acell = A1 - A0 \quad \text{[Expression 4]}$$

where A1 is the absorbance at the time of the first light amount measurement, and A0 is the absorbance at the time of the water light amount measurement in normal state during calibration measurement.

Using the absorbance Acell according to Expression 4 enables the transmittance of the reaction cell Tcell to be expressed as $$Tcell = 10^{\wedge}(-(Acell) \times L/L') \quad \text{[Expression 5]}$$

where L is the optical path length of the reaction solution at the time of actual measurement and may be 5 mm, for example, and L' is the optical path length when calculating the absorbance and may be 10 mm in the field of automatic analysis device.

The content of data processing executed when estimating the transmittance and the amount of scattered light of the disturbance substance in the sample from the light measurement values at the time of the second light amount measurement will be described. Herein, the amount of scattered light from the disturbance substance in the sample is Ssample, and the transmittance thereof is Tsample.

The scattered light amount Scell from the reaction cell is attenuated by the disturbance substance included in the sample, while the scattered light Ssample from the disturbance substance in the sample is attenuated by the reaction cell. Accordingly, the scattered light amount Is2 at the time of the second light amount measurement (FIG. 4) is expressed as follows.

$$Is2 = Scell \times Tsample + Ssample \times Tcell \quad \text{[Expression 6]}$$

Transforming Expression 6 with respect to the scattered light amount Ssample of the sample, we have $$Ssample = (Is2 - Scell \times Tsample)/Tcell \quad \text{[Expression 7]}$$

where Scell and Tcell are values that can be computed from the values at the time of the first light amount measurement according to Expression 2 and Expression 3 or Expression 5.

A technique for computing the transmittance Tsample of the sample will be described. Using the transmitted light amount It1 at the time of the water blank measurement and the transmitted light amount It2 at the time of the S+R1 measurement, the transmittance Tsample of the sample can be computed as follows.

$$Tsample = It2/It1 \quad \text{[Expression 8]}$$

As a result, all of the values on the right side of Expression 7 are provided, whereby the scattered light amount Ssample of the sample can be approximately calculated.

The transmittance Tsample of the sample may also be determined from the absorbance A2 at the time of the second light amount measurement and the absorbance A1 at the time of the first light amount measurement according to the separately prepared absorptiometer. In this case, the absorbance Asample of the sample can be computed as follows.

$$Asample = A2 - A1 \quad \text{[Expression 9]}$$

Using the absorbance Asample according to Expression 9 enables computation of the transmittance Tsample of the sample as follows.

$$Tsample = 10^{\wedge}(-(Asample) \times L/L') \quad \text{[Expression 10]}$$

The content of data processing for removing, from the light measurement values at the time of the third and the fourth light amount measurements, the influence of the amount of scattered light from the reaction cell and the sample, and for approximately calculating the amount of scattered light from the latex particles will be described.

At the time of the third and the fourth light amount measurements, the amounts of scattered light Is3 and Is4 produced in the reaction cell and the transmittance of the reaction cell do not change, whereas the concentration of the disturbance substance present in the sample is decreased by an increase in the amount of the reaction solution due to the dispensing of the second reagent. Thus, the amount of scattered light due to the disturbance substance in the sample and the transmittance are varied.

Herein, when the amount of the reaction solution at the time of the second light amount measurement is V2, the amount of the reaction solution at the time of the third and the fourth light amount measurements is V3, and a liquid amount coefficient K=V2/V3, the disturbance substance concentration included in the sample is diluted by a factor of K. At this time, the amount Ssample' of scattered light from the disturbance substance in the sample at the time of the third and the fourth light amount measurements is expressed as follows.

$$\text{Ssample}' = \text{Ssample} \times K \quad \text{[Expression 11]}$$

Then, when the absorbance of the disturbance substance in the sample at the time of the third and the fourth light amount measurements is Asample', since the absorbance is proportional to the concentration, the absorbance is expressed as follows.

$$\text{Asample}' = \text{Asample} \times K \quad \text{[Expression 12]}$$

Herein, the transmittance Tsample' of the disturbance substance in the sample at the time of the third and the fourth light amount measurements can be expressed, with reference to Expression 10, as follows.

$$\begin{aligned}
Tsample' &= 10^{\wedge}(-(Asample') \times L/L') \quad \text{[Expression 13]} \\
&= 10^{\wedge}(-(Asample) \times K \times L/L') \\
&= 10^{\wedge}(\log(It2/It1) \times K) \\
&= (It2/It1)^{\wedge}K \\
&= (It2/It1)^{\wedge}(V2/V3)
\end{aligned}$$

Further, when the amount of scattered light from the latex particles prior to agglutination reaction is Slatex3 and the transmittance is Tlatex3, and the amount of scattered light from the latex particles after agglutination reaction is Slatex4 and the transmittance is Tlatex4, following expressions are obtained.

$$Tlatex3 = It3/It2 \quad \text{[Expression 14]}$$

$$Tlatex4 = It4/It2 \quad \text{[Expression 15]}$$

Alternatively, Tlatex3 and Tlatex4 may be calculated from the amount of transmitted light at the time of the second light amount measurement and the amount of transmitted light and the absorbance at the time of the third light amount measurement during calibration measurement, instead of according to the above expressions.

From the above expressions, the scattered light amounts Is3 and Is4 at the time of the third and the fourth light amount measurements can be expressed as follows.

$$\begin{aligned}
Is3 = &\; Scell \times Tsample' \times Tlatex3 + \\
&\; Ssample' \times Tcell \times Tlatex3 + \\
&\; Slatex3 \times Tcell \times Tsample'
\end{aligned} \quad \text{[Expression 16]}$$

$$\begin{aligned}
Is4 = &\; Scell \times Tsample' \times Tlatex4 + \\
&\; Ssample' \times Tcell \times Tlatex4 + \\
&\; Slatex4 \times Tcell \times Tsample'
\end{aligned} \quad \text{[Expression 17]}$$

Transforming Expression 16 and Expression 17 so as to determine the scattered light amounts Slatex3 and Slatex4 from the latex particles as the substance to be measured, we have the followings.

$$Slatex3 = (Is3 - Scell \times Tsample' \times Tlatex3 - Ssample' \times Tcell \times Tlatex3)/(Tcell \times Tsample') \quad \text{[Expression 18]}$$

$$Slatex4 = (Is4 - Scell \times Tsample' \times Tlatex4 - Ssample' \times Tcell \times Tlatex4)/(Tcell \times Tsample') \quad \text{[Expression 19]}$$

Herein, Slatex4−Slatex3 is computed so as to calculate a corrected operation value ΔI' for the case where the influence of disturbance substance is large.

$$\begin{aligned}
\Delta I' = &\; Slatex4 - Slatex3 = \\
&\; (Is4 - Scell \times Tsample' \times Tlatex4 - Ssample' \times Tcell \times \\
&\; Tlatex4 - Is3 + Scell \times Tsample' \times Tlatex3 + \\
&\; Ssample' \times Tcell \times Tlatex3)/(Tcell \times Tsample')
\end{aligned} \quad \text{[Expression 20]}$$

By applying the calculated value to the calibration curve, the concentration of the latex particles can be quantitated.

In the following, a method for simplifying the above computations will be described. By using a simplified computing expression, the concentration of the latex particles can be quantitated from the measured values without putting a burden on a data processing unit of the automatic analysis device.

Simplified Example 1

The amount of scattered light from the disturbance substance in the reaction cell and the sample is smaller than the amount of scattered light from the latex particles and can in many cases be disregarded. When that condition is satisfied, it can be considered that Scell=0 and Ssample'=0. In this case, Expression 18 for calculating the amount of scattered light of the latex particles from the amount of scattered light at the time of the third light amount measurement, for example, can be simplified as follows.

$$Slatex3 = Is3/(Tcell \times Tsample') \quad \text{[Expression 21]}$$

Herein, applying Expression 3 and Expression 13 to Expression 21 enables Expression 21 to be expressed as follows.

$$Slatex3 = Is3/((It1/It0) \times ((It2/It1)^{\wedge}(V2/V3))) \quad \text{[Expression 22]}$$

Of course, the scattered light amount Slatex4 at the time of the fourth light amount measurement can also be expressed by a similar expression.

Thus, the corrected operation value ΔI' given by Expression 20 can be expressed as follows.

$$\Delta I' = (Is4 - Is3)/((It1/It0) \times ((It2/It1)^{\wedge}(V2/V3))) \quad \text{[Expression 23]}$$

Simplified Example 2

The reaction cell is separately managed using an absorptiometer and the like, and is often not used for sample measurement when contaminated more than a certain level. Thus, in reality, the influence of light attenuation by the reaction cell can be in many cases disregarded. In that case, it can be considered that Tcell=1, Scell=0, and Ssample'=0. In this case, Expression 18 can be simplified as follows.

$$Slatex3 = Is3/((It2/It1)^{\wedge}(V2/V3)) \quad \text{[Expression 24]}$$

Of course, Expression 19 can be simplified in a similar form.

In this case, the corrected operation value ΔI' given by Expression 20 can be expressed as follows.

$$\Delta I' = (Is4 - Is3)/((It2/It1)^{\wedge}(V2/V3)) \quad \text{[Expression 25]}$$

Simplified Example 3

Generally, because the reaction cell contamination and the like are managed using the absorptiometer and the like, the influence of light attenuation by the reaction cell or that of scattered light in the reaction cell may be disregarded. However, if the probability is high that the sample includes disturbance substance, it is better to be able to correct for its influence. In this case, because it can be considered that Tcell=1 and Scell=0, Expression 7 can be simplified as follows.

$$Ssample = Is2 \qquad \text{[Expression 26]}$$

In this case, Expression 18 can be simplified as follows.

$$\begin{aligned}Slatex3 &= (Is3 - Ssample' \times Tlatex3)/((It2/It1)^{\wedge}(V2/V3)) \\ &= (Is3 - Is2 \times (V2/V3) \times It3/It2)/((It2/It1)^{\wedge}(V2/V3))\end{aligned} \qquad \text{[Expression 27]}$$

Of course, Expression 19 can be simplified in a similar form.

In this case, the correction operation value ΔI' given by Expression 20 is expressed as follows.

$$\Delta I' = (Is4 - Is2 \times (V2/V3) \times It4/It2 - Is3 + Is2 \times (V2/V3) \times It3/It2)/((It2/It1)^{\wedge}(V2/V3)) \qquad \text{[Expression 28]}$$

In this case, a correction operation that does not disregard the influence of disturbance substance included in the sample can be executed without putting a burden on the data processing unit of the automatic analysis device.

Simplified Example 4

More simply, instead of correcting the operation value or the amount of light as described above, the concentration quantitated from the measured values may be corrected. For example, if the condition is the same as in the case of Expression 21, the concentration C' after correction may be calculated using the uncorrected concentration C determined from the uncorrection operation value ΔI as follows.

$$C' = C/(Tcell \times Tsample') \qquad \text{[Expression 29]}$$

It is also noted that Expression 29 may be expressed, using Expression 3 and Expression 13, as follows.

$$C' = C/\{(It1/It0) \times ((It2/It1)^{\wedge}(V2/V3))\} \qquad \text{[Expression 30]}$$

However, this correction operation is effective in a concentration range where the intercept of the calibration curve is near zero and where the operation value and the concentration value can be considered to have an approximately proportional relationship. This computing technique is effective in that not much time and effort is required for computing and the analysis speed is high.

(Conclusion)

As described above, by adopting the data processing technique proposed in the present Description, even in the presence of a plurality of scattering bodies, the amount of scattered light from each scattering body can be approximately calculated and the true amount of scattered light of the substance to be measured can be calculated.

Example 1

In the present example, the basic configuration of the automatic analysis device and the outline of a correction method will be described, the device being equipped with the function for calculating a correction value in the presence of disturbance substance other than the substance to be measured, such as reaction cell contamination or scratches, foreign matter in the sample, or fat globule that turns to a chylous state, during scattered light measurement.

Figure 6:
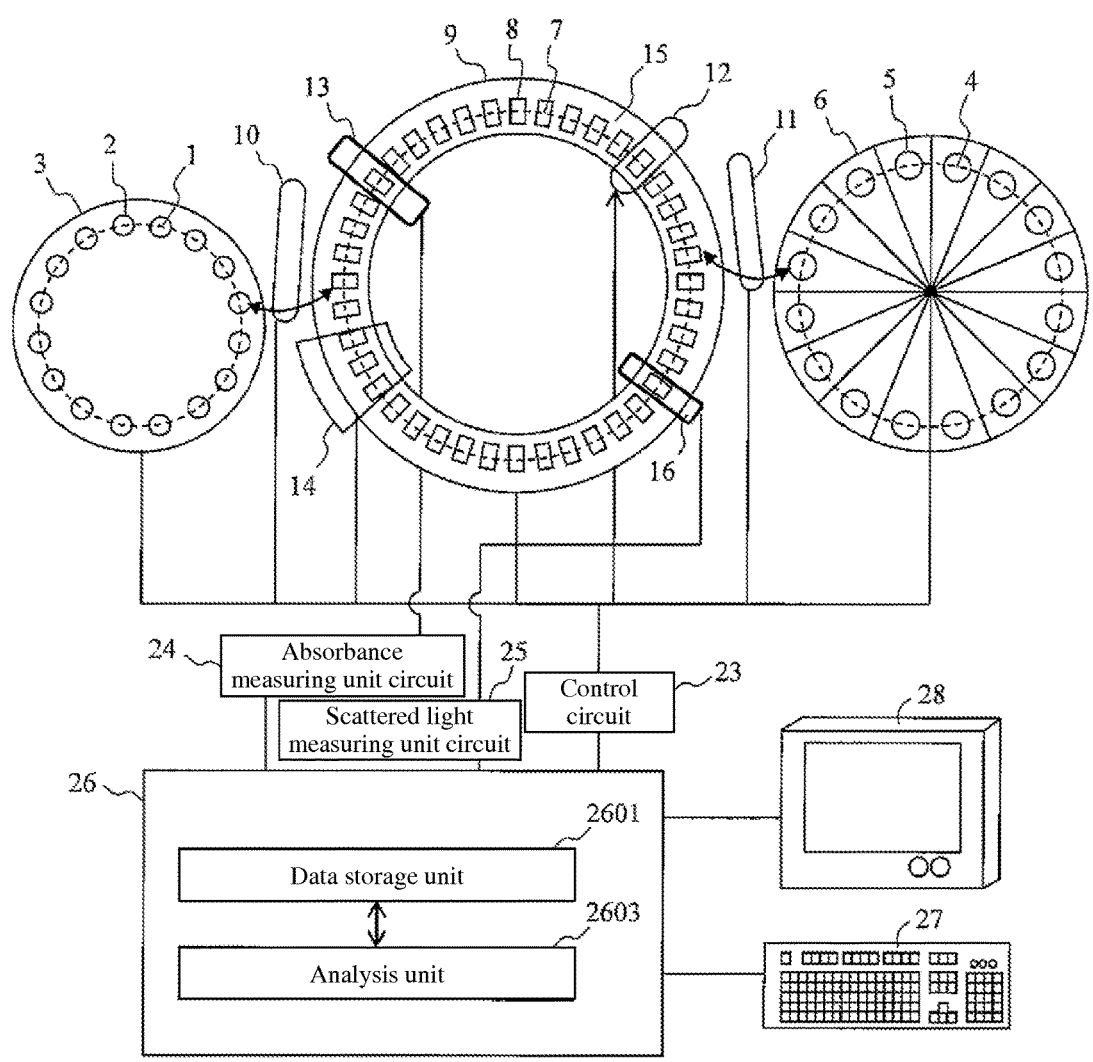
FIG. 6 is a diagram of an overall configuration example of an automatic analysis device according to an example.

FIG. 6 illustrates an overall configuration example of the automatic analysis device according to the present example. The automatic analysis device according to the present example is configured from: three types of discs of a sample disc 3, a reagent disc 6, and a reaction disc 9; a dispensing mechanism that moves the sample or reagent between the discs; a control circuit 23 that controls the above; an absorbance measuring unit circuit 24 that measures the absorbance of a reaction solution; a scattered light measuring unit circuit 25 that measures scattered light from the reaction solution; a data processing unit 26 that processes data measured by each measuring unit circuit; and an input unit 27 and an output unit 28 providing an interface with the data processing unit 26.

The data processing unit 26 is configured from a data storage unit 2601 and an analysis unit 2603. In the data storage unit 2601, there are stored control data, measurement data, data used for data analysis, analysis result data and the like. The input unit 27 and the output unit 28 are used for data input and output with the data storage unit 2601. In the example of FIG. 6, the input unit 27 is illustrated as being a keyboard; however, it may include a touch panel, a numeric keypad, or other input devices.

On the circumference of the sample disc 3, a plurality of sample cups 2 providing containers for a sample 1 are disposed. The sample 1 is blood, for example. On the circumference of the reagent disc 6, a plurality of reagent bottles 5 providing containers for a reagent 4 are disposed. On the circumference of the reaction disc 9, a plurality of reaction cells 8 providing containers for a reaction solution 7 including the sample 1 and the reagent 4 mixed therein are disposed.

The sample dispensing mechanism 10 is a mechanism used for moving an amount of the sample 1 from the sample cup 2 to the reaction cells 8. The sample dispensing mechanism 10 is configured from, for example, a nozzle for discharging or suctioning a solution; a robot for positioning and transporting the nozzle to a predetermined position; and a pump for discharging the solution via the nozzle or suctioning the solution into the nozzle.

The reagent dispensing mechanism 11 is a mechanism used for moving a certain amount of the reagent 4 from the reagent bottles 5 to the reaction cells 8. The reagent dispensing mechanism 11 is also configured from, for example, a nozzle for discharging or suctioning a solution; a robot for positioning and transporting the nozzle to a predetermined position; and a pump for discharging the solution via the nozzle or suctioning the solution into the nozzle.

A stirring unit 12 is a mechanism unit for stirring and mixing the sample 1 and the reagent 4 in the reaction cells 8. A washing unit 14 is a mechanism unit for discharging the reaction solution 7 from the reaction cells 8 after an analysis process and thereafter washing the reaction cells 8. Into the reaction cells 8 that have been washed, a next sample 1 is again dispensed from the sample dispensing mechanism 10 and a new reagent 4 is dispensed from the reagent dispensing mechanism 11 so that the cells can be used for another reaction process.

In the reaction disc 9, the reaction cells 8 are immersed in a constant-temperature fluid 15 in a constant-temperature bath with controlled temperature and flow rate. Accordingly, the reaction cells 8 and the reaction solution 7 therein are maintained at a constant temperature even when being moved by the reaction disc 9. In the present example, water is used as the constant-temperature fluid 15, and its temperature is adjusted to 37±0.1° C. by the control circuit 23. Of course, the medium used as the constant-temperature fluid 15 and its temperature herein are exemplary.

At parts of the circumference of the reaction disc 9, an absorbance measuring unit (absorptiometer) 13 and a scattered light measuring unit (light-scattering photometer) 16 are disposed.

Figure 7:
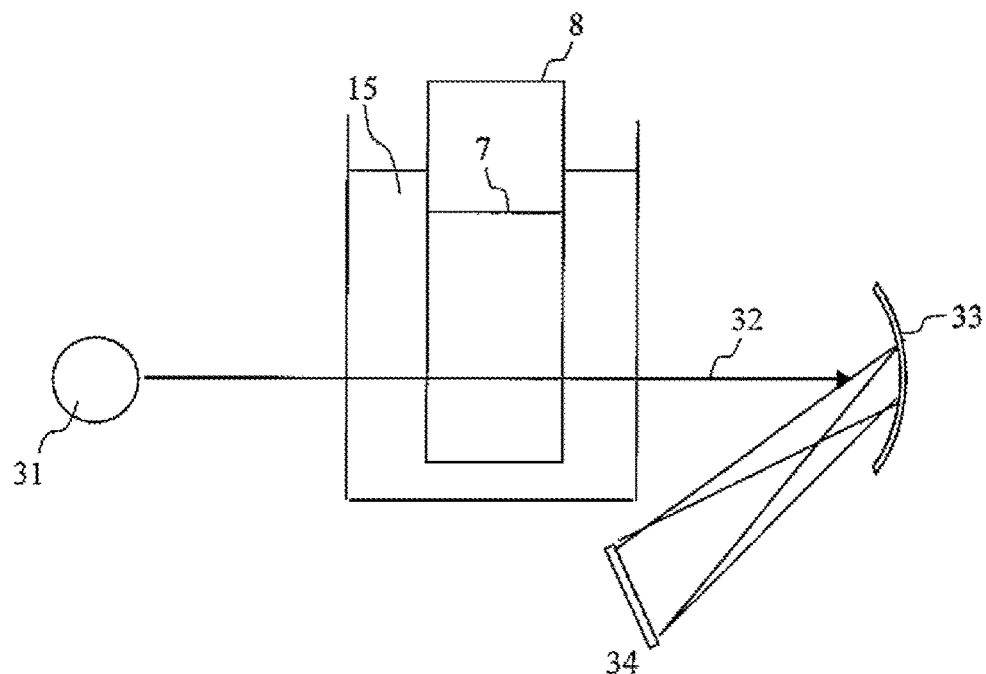
FIG. 7 is a diagram of a schematic configuration example of an absorbance measuring unit.

FIG. 7 illustrates a configuration example of the absorbance measuring unit 13. The absorbance measuring unit 13 illustrated in FIG. 7 is structured to irradiate the reaction cells 8 with light emitted from a halogen lamp light source 31, and to separate the light that has passed through the reaction cells 8 (transmitted light 32) into spectral components by a diffraction grating 33 before receiving the light with a photodiode array (an absorbance measurement light receiving unit 34). The wavelengths received by the photodiode array (the absorbance measurement light receiving unit 34) are 340 nm, 405 nm, 450 nm, 480 nm, 505 nm, 546 nm, 570 nm, 600 nm, 660 nm, 700 nm, 750 nm, and 800 nm. Light reception signals from the light receiving units are transmitted via the absorbance measuring unit circuit 24 to the data storage unit 2601 of the data processing unit 26. Herein, the absorbance measuring unit circuit 24 acquires the light reception signals of the wavelength ranges at regular periods, and outputs the acquired light amount values to the data processing unit 26.

Figure 8:
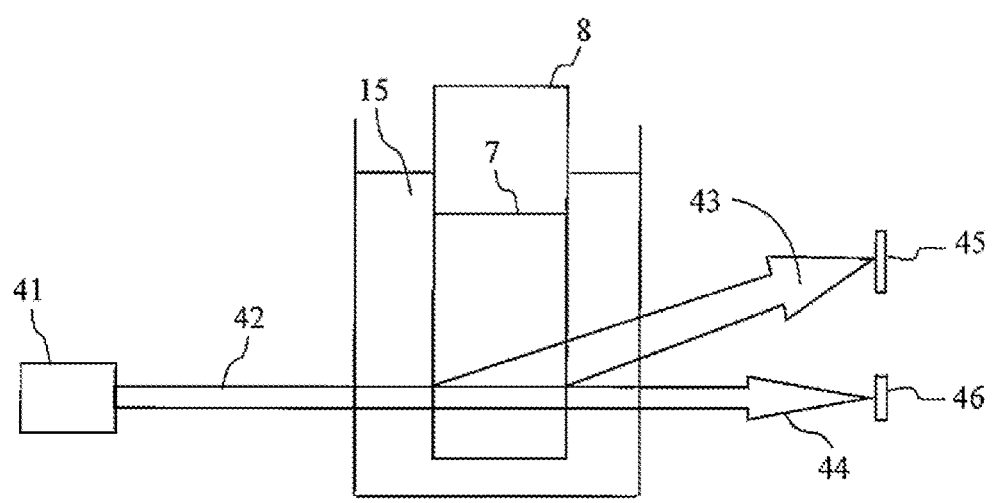
FIG. 8 is a diagram of a schematic configuration example of a scattered light measuring unit.

FIG. 8 illustrates a configuration example of the scattered light measuring unit 16. In the case of the present example, as the light source 41, an LED light source unit and the like is used, for example. The LED light source unit emits irradiation light 42 which irradiates the reaction cells 8 positioned on the optical path of the light, and transmitted light 44 that has passed through the reaction cells 8 is received by a transmitted light receiving unit 46. As the wavelength of the irradiation light, 700 nm is used, for example. While in the present example, the LED light source unit is used as the light source 41, a laser light source, a xenon lamp, a halogen lamp and the like may be used.

The scattered light measuring unit 16 receives the scattered light 43 in a direction away from the optical axis of the irradiation light 42 or the transmitted light 44 by a predetermined angle (such as 20° in air), using a scattered light receiving unit 45. The scattered light receiving unit 45 is configured from photodiodes, for example. Light reception signals from the scattered light receiving unit 45 are transmitted via the scattered light measuring unit circuit 25 to the data storage unit 2601 of the data processing unit 26.

The scattered light receiving unit 45 is disposed in a plane generally perpendicular to the direction in which the reaction cells 8 are moved by rotation of the reaction disc 9. Herein, the reference position for the light reception angle (the starting point of scattering) is set at the center of the optical path of the light passing through the reaction cells 8.

While the case has been described with reference to FIG. 8 in which the scattered light receiving unit 45 is disposed at the light reception angle of 20°, a single linear array containing a number of light receiving units may be disposed and configured to receive some of the scattered light. Using the linear array provides more choices of the light reception angle. Instead of the scattered light receiving unit 45, an optical system of fibers and lenses and the like may be disposed to guide the light to a scattered light receiving unit disposed at a separate location.

The quantitation of the concentration of a component included in the sample 1 is performed according to the following procedure. First, the control circuit 23 causes the washing unit 14 to wash the reaction cells 8. The control circuit 23 then causes the sample dispensing mechanism 10 to dispense a certain amount of the sample 1 in the sample cup 2 into the reaction cells 8. Then, the control circuit 23 causes the reagent dispensing mechanism 11 to dispense a certain amount of the reagent 4 in the reagent bottles 5 into the reaction cells 8.

At the time of dispensing each solution, the control circuit 23 causes the sample disc 3, the reagent disc 6, and the reaction disc 9 to be rotated by respectively corresponding drive units. At this time, the sample cup 2, the reagent bottles 5, and the reaction cells 8 are positioned at predetermined dispensing positions in accordance with the drive timing of the corresponding dispensing mechanisms.

Thereafter, the control circuit 23 controls the stirring unit 12 to stir the sample 1 and the reagent 4 dispensed into the reaction cells 8, producing the reaction solution 7. As the reaction disc 9 rotates, the reaction cells 8 holding the reaction solution 7 pass the measurement position at which the absorbance measuring unit 13 is disposed and the measurement position at which the scattered light measuring unit 16 is disposed. Every time the reaction cells pass each measurement position, the transmitted light or scattered light from the reaction solution 7 is measured by the respectively corresponding absorbance measuring unit 13 or the scattered light measuring unit 16. In the case of the present example, the respective measurement time is approximately 10 minutes. Measurement data obtained by the absorbance measuring unit 13 and the scattered light measuring unit 16 are successively output to the data storage unit 2601 and accumulated therein as reaction process data.

During the accumulation of the reaction process data, a separate reagent 4 may be additionally dispensed as needed into the reaction cells 8 by the reagent dispensing mechanism 11, stirred by the stirring unit 12, and then measured for a certain time. In this way, the reaction process data acquired at regular time intervals are stored in the data storage unit 2601.

Examples of the reaction process data are as illustrated in FIG. 2, FIG. 4, and FIG. 5. The light measurement points shown on the horizontal axis of FIG. 2, FIG. 4, and FIG. 5 indicate the sequence of measurement of the reaction process data. The analysis unit 2603 calculates, as the operation value, a change in the light amount in a certain time designated through an analysis setting screen, which is not illustrated. Herein, the certain period used for calculating the operation value is defined by designating an operation start point and an operation end point from the light measurement points. The operation value is computed as a difference in the amount of light between the operation start point and the operation end point.

In the data storage unit 2601, calibration curve data indicating the relationship between the operation value here and the measured substance concentration are retained in advance. The analysis unit 2603 compares the computed operation value with the calibration curve data, and quantitates the concentration of the measured substance. The quantitated concentration value is displayed via the output unit 28.

The analysis unit 2603 also computes a correction value and stores it in the data storage unit. The analysis unit 2603, if the calculated correction value does not satisfy a predetermined condition with the concentration value before correction in the data storage unit, determines that the quantitation result is a measurement abnormality including the influence of foreign matter reaction. The determination result is also stored in the data storage unit 2601. In this case, the analysis unit 2603 displays an alarm on the user interface screen together with the quantitation value, and also displays the correction value for reference.

The data necessary for the control of the various units and analysis are input from the input unit 27 to the data storage unit 2601. The various data stored in the data storage unit 2601, measurement results, analysis results, alarms and the like are displayed on the user interface screen by the output unit 28.

[Analysis Setting Screen]

Figure 9:
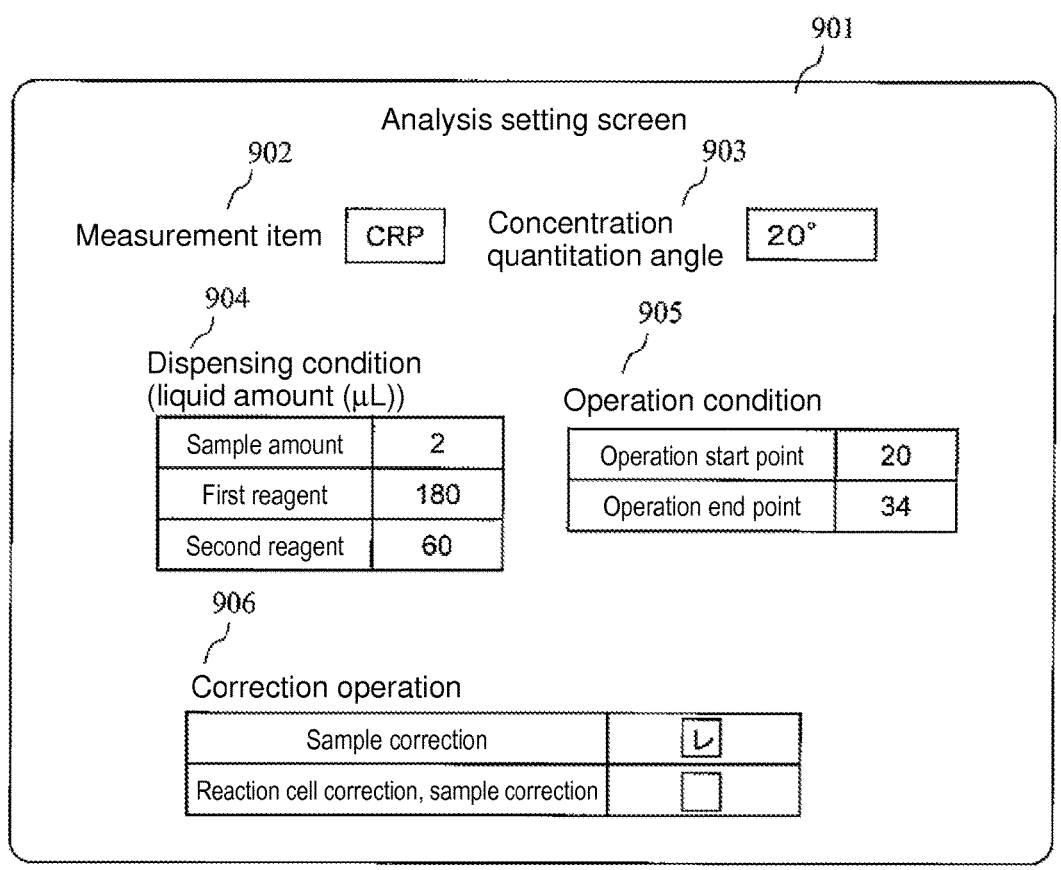
FIG. 9 is a diagram of an example of an analysis setting screen.

FIG. 9 illustrates an example of an analysis setting screen as part of the user interface screen. The user, by using the analysis setting screen 901, sets a concentration measurement angle 903, a dispensing condition 904, an operation condition 905, and a correction operation condition 906 for each measurement item 902. In the example of FIG. 9, the measurement item 902 is PGI (pepsinogen I). In the example of FIG. 9, the concentration measurement angle 903 is 20°. Further, in the example of FIG. 9, the dispensing condition 904 indicates that the sample amount is 2 μL, the first reagent is 180 μL, and the second reagent is 60 μL.

FIG. 9 also indicates that, as the operation condition 905, the operation start point is set at the 20th measurement point, and the operation end point is set at the 34th measurement point. Accordingly, in the case of FIG. 9, the analysis unit 2603 determines the operation value from a change in the amount of light that is measured during a reaction in the certain time from the 20th measurement point to the 34th measurement point.

FIG. 9 also indicates that, as the correction operation condition 906, correction for only the sample influence or correction for both the sample influence and the reaction cell influence can be selected by checking in the check boxes. This is in view of the fact that in many cases, the reaction cell is managed. A check box for selecting correction for only the reaction cell influence may be provided. If the correction for both the sample influence and the reaction cell influence is selected, a value corrected for the sample influence and a value corrected for the reaction cell influence are both calculated and displayed. In this case, it can be displayed whether the influence of disturbance factor due to the sample or the influence of disturbance factor due to the reaction cell is larger. Alternatively, one correction value corrected for the sample influence and the reaction cell influence both simultaneously may be computed and displayed.

The correction operation condition 906 may be manually input by the user with reference to a method recommended by the manufacturer of each reagent. The automatic analysis device may be provided with the function for automatically setting the correction operation condition 906, so that a setting recommended for each reagent by the reagent manufacturer can be automatically set.

The user designates, via a separate screen which is not illustrated, the corresponding relationship of the sample number of the blood to be measured and the sample position in the sample disc, and also designates the examination item.

[Processing Operation of the Automatic Analysis Device]

Figure 10:
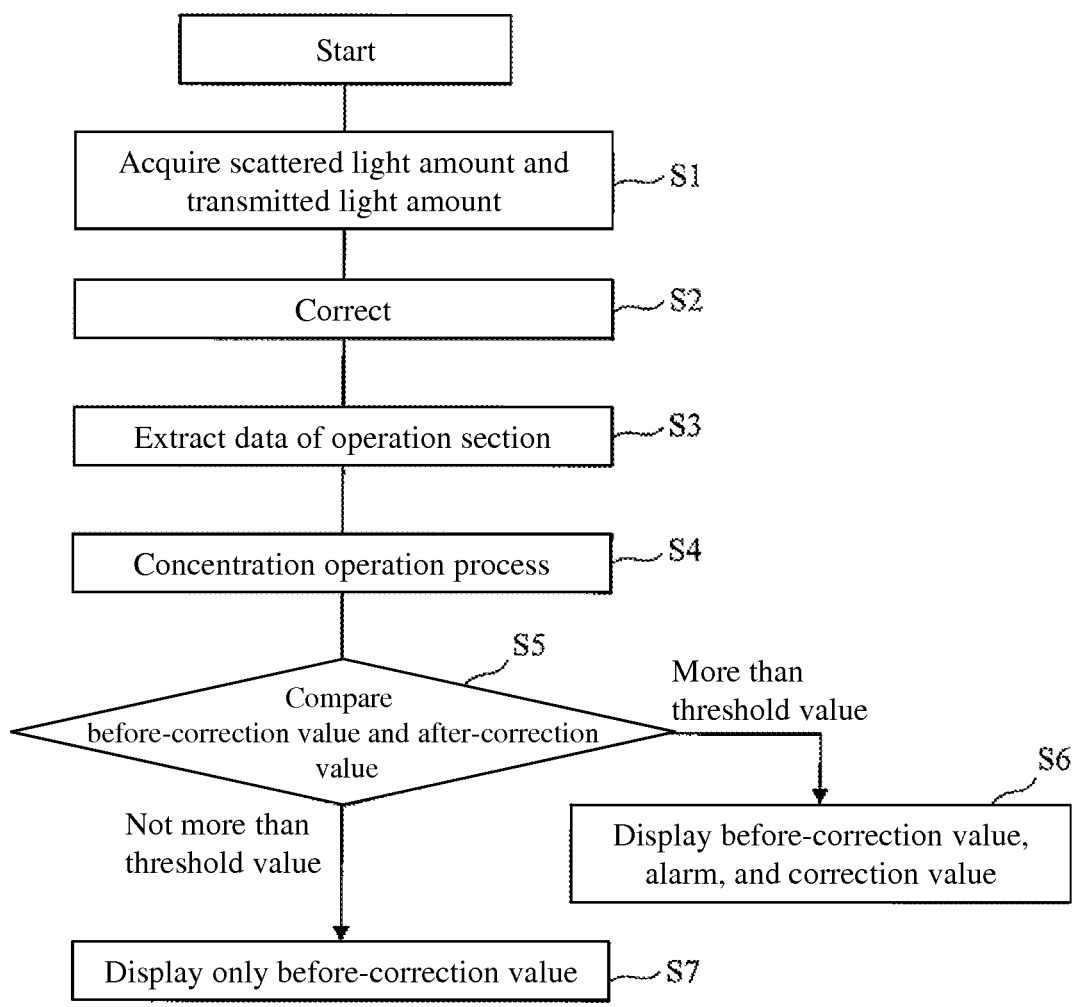
FIG. 10 is a flowchart of a data processing procedure executed in the automatic analysis device according to the example.

FIG. 10 illustrates an example of a processing operation executed by the automatic analysis device according to the example. FIG. 10 indicates a series of processing operations from the start of the concentration measurement by the operation automatic analysis device to the display of the quantitation result.

As preprocessing, the control circuit 23 determines whether the analysis conditions and examination items have been set. Upon confirming the setting of the analysis conditions and examination items, the control circuit 23 controls the various units of the automatic analysis device, and starts measurement of the concentration of a predetermined sample (the concentration of the substance to be measured) designated by the user. As the measurement starts, the scattered light strength is measured at each light reception angle, and the measured scattered light strengths are stored in the data storage unit 2601 as time-series data (i.e., reaction process data) (step S1).

The analysis unit 2603 then corrects the measured strength values in accordance with the set conditions designated in the correction operation setting 906 in the analysis setting screen 901, for example (step S2). In this case, the analysis unit 2603 extracts data with respect to a section designated by the operation condition 905 in the analysis setting screen 901 (step S3), and computes a concentration on the basis of the extracted data (step S4). Specifically, the difference ΔI' between the light measurement value at the time of the third light amount measurement and the light measurement value at the time of the fourth light amount measurement is applied to the calibration curve to compute the concentration. Alternatively, after the concentration C is computed with respect to the light measurement value prior to correcting the measured strength value, the concentration C' corrected for the disturbance factor according to Expression 29 may be computed.

Then, the analysis unit 2603 determines whether the difference or ratio of the before-correction value and the after-correction value is not more than a threshold value (step S5). If the after-correction value is greater than the threshold value, the analysis unit 2603 displays, via the output unit 28, an alarm indicating that the influence of disturbance substance is large and the correction value on the screen, together with the quantitation result (step S6).

On the other hand, if the before-correction value and the after-correction value are not greater than the threshold value, the analysis unit 2603 displays the before-correction value (concentration value) on the screen as the quantitation result (step S7). The screen may also simultaneously display the absence of the influence of foreign matter reaction in the quantitation result, or an operation value ratio (scattered light strength ratio).

Figure 11:
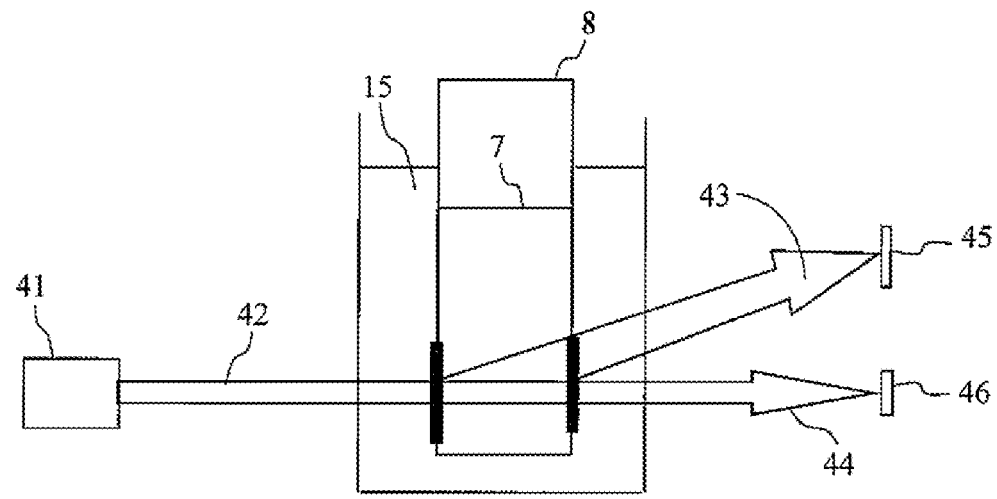
FIG. 11 is a diagrammatic representation of the measuring by the scattered light measuring unit at the time of the water blank measurement during measurement with a large influence of disturbance factor.

FIG. 11 illustrates the outline of a scattered light measurement unit at the time of the water blank measurement during measurement with a large influence of disturbance. At the point in time of the water blank measurement, there is only water in the reaction cells 8. Accordingly, the scattered light receiving unit 45 receives scattered light from the reaction cells.

Figure 12:
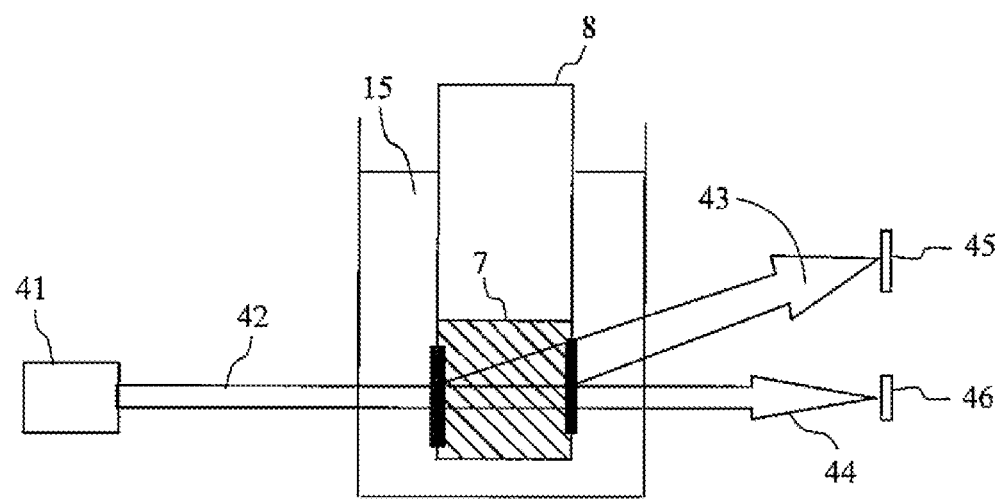
FIG. 12 is a diagrammatic representation of the measuring by the scattered light measuring unit at the time of S+R1 measurement during measurement with a large influence of disturbance factor.

FIG. 12 illustrates the outline of the scattered light measurement unit at the time of the S+R1 measurement during measurement with a large influence of disturbance. In this case, the scattered light receiving unit 45 receives the mixture of light from the reaction cell and light from the sample in a chylous state due to disturbance substance in the sample, such as fat globules.

Figure 13:
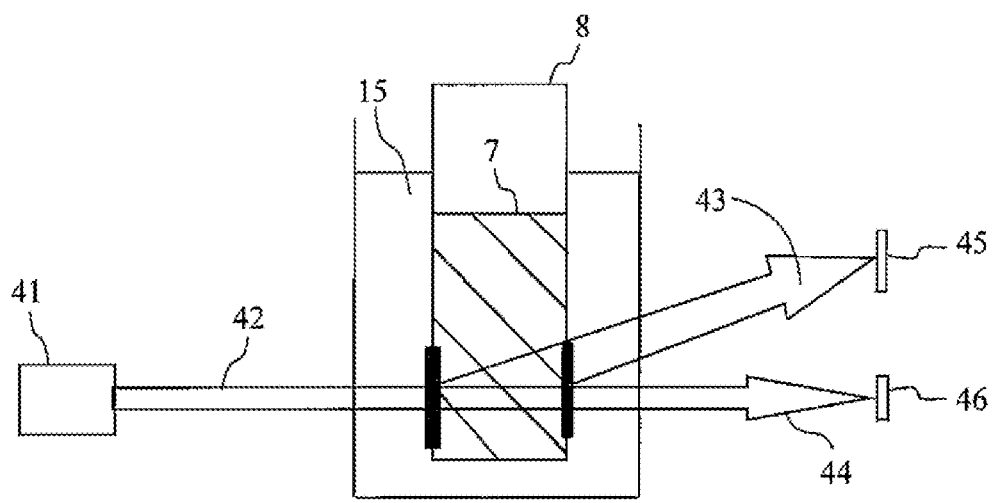
FIG. 13 is a diagrammatic representation of the measuring by the scattered light measuring unit at the time of S+R1+R2 measurement during measurement with a large influence of disturbance factor.

FIG. 13 illustrates the outline of the scattered light measuring unit at the time of S+R1+R2 measurement during measurement with a large influence of disturbance. In this case, the scattered light receiving unit 45 receives the mixture of light from the reaction cell and light from fat globules and latex reagents included in the sample. Because the agglutination reaction proceeds in a time period on the order of 5 minutes, the component amount of the substance to be measured that is included in the sample is quantitated from a change in the light amount during that period. Examples of the reaction process in such states are similar to those illustrated in FIG. 4 and FIG. 5.

Figure 14:
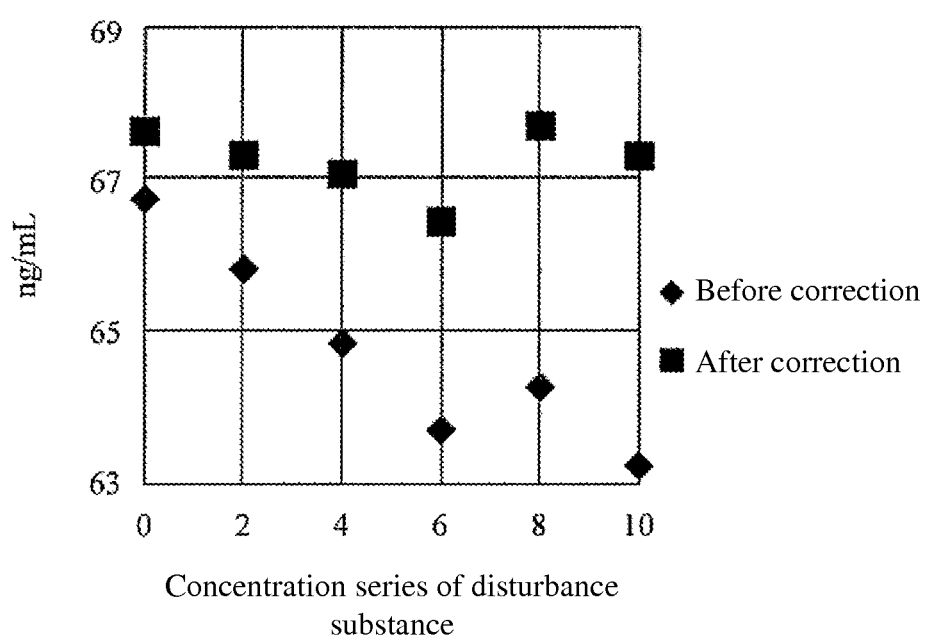
FIG. 14 is a diagram for describing the relationship between sample concentration value before correction and sample concentration value after correction.

FIG. 14 illustrates an example of the correction result of the quantitation value. In FIG. 14, the concentration series of the disturbance substance included in the sample is shown on the horizontal axis, and the component amount of a certain substance to be measured is shown on the vertical axis. In the figure, the black rhombuses indicate the before-correction quantitation values, while the black squares indicate the after-correction quantitation values. From FIG. 14, it can be seen that, even when the concentration of the disturbance substance included in the sample is increased, the component amount can be accurately quantitated by using the correction operation proposed in the present Description.

FIG. 15 illustrates an example of a measurement result screen 1501 displayed on the output unit 28 of the automatic analysis device according to the example. On the measurement result screen 1501 illustrated in FIG. 15, a specimen number 1502, a specimen position 1503, and a quantitation result 1504 are displayed. In the case of the present example, the quantitation result 1504 is configured from an examination item, a quantitation result, and an after-correction quantitation result in such a way that the quantitation result before and after correction can be confirmed within the same screen with respect to the sample for which measured value correction was necessary. Thus, because the quantitation results before and after correction can be confirmed simultaneously within the same screen, the values before and after correction can be easily compared.

[Conclusion]

According to the present example, during concentration measurement of a sample by scattered light measurement, even when the reaction cell has scratches or contamination and/or the sample includes fat globules or fibrin clot, the scattered light from the latex particles which are the substance to be measured can be accurately computed and their concentration can be quantitated.

Other Examples

The present invention is not limited to the above-described example and may include various modifications. The example has been described in detail for facilitating an understanding of the present invention, and is not limited to include all of the described configurations. A part of one example may be substituted by another configuration, or the configuration of the other example may be incorporated into the configuration of the one embodiment. A part of the configuration of one example may be substituted by another configuration.

The various configurations, functions, processing units, processing means and the like may be partly or entirely implemented in the form of an integrated circuit or other hardware. The various configurations, functions and the like may be implemented by a processor interpreting and executing a program for implementing the respective functions; i.e., in the form of software. The information of the programs, tables, files and the like for implementing the functions may be stored in a storage device such as a memory, a hard disk, or a SSD (Solid State Drive), or in a storage medium such as an IC card, an SD card, or a DVD.

The control lines and information lines shown are those considered necessary for the purpose of description, and do not represent all of the control lines or information lines required in a product. It may be considered that in practice, almost all of the configurations are mutually connected.

REFERENCE SIGNS LIST

1 Sample
2 Sample cup
3 Sample disc
4 Reagent
5 Reagent bottle
6 Reagent disc
7 Reaction solution
8 Reaction cell
9 Reaction disc
10 Sample dispensing mechanism
11 Reagent dispensing mechanism
12 Stirring unit
13 Absorbance measuring unit
14 Washing unit
15 Constant-temperature fluid
16 Scattered light measuring unit
23 Control circuit
24 Absorbance measuring unit circuit
25 Scattered light measuring unit circuit
26 Data processing unit
2601 Data storage unit
2603 Analysis unit
27 Input unit
28 Output unit
31 Light source
32 Transmitted light
33 Diffraction grating
34 Absorbance measurement light receiving unit
41 Light source
42 Irradiation light
43 Scattered light
44 Transmitted light
45 Scattered light receiving unit
46 Transmitted light receiving unit

The invention claimed is:

1. An automatic analysis device comprising:
a scattered light measuring unit that measures an amount of scattered light obtained from light irradiation of a reaction cell;
a transmitted light measuring unit that measures an amount of transmitted light obtained from the light irradiation of reaction cell;
a data storage unit that stores data of the measured amounts of scattered light and transmitted light; and
an analysis unit that programmed to compute, based on the measured amounts of scattered light and transmitted light, a concentration of a substance to be measured included in a sample in the reaction cell with respect to an examination item,
wherein the scattered light measuring unit and the transmitted light measuring unit perform:
a first light amount measurement of the scattered light and the transmitted light with water dispensed in the reaction cell before the sample is dispensed therein,
a second light amount measurement of the scattered light and the transmitted light after the sample and a pre-processing reagent are dispensed into the reaction cell,
a third light amount measurement of the scattered light and the transmitted light after a reaction reagent is dispensed into the reaction cell and before the reaction reagent and the substance to be measured react with each other, and
a fourth light amount measurement of the scattered light and the transmitted light after the reaction reagent and the substance to be measured have reacted,
and
wherein the analysis unit is further programmed to correct, based on the measured amounts at the first and the second light amount measurements and a liquid amounts in the reaction cell at each of the second and the third light amount measurements, the measured amount of scattered light at the third light amount measurement and the measured amount of scattered light at fourth light amount measurement, and is further programmed to compute the concentration based on the corrected amounts of the scattered light at the third and the fourth light amount measurements.

2. The automatic analysis device according to claim 1, wherein the analysis unit is further programmed to compute the concentration based on Slatex3 which is the corrected amount of the scattered light at the third light amount measurement and Slatex4 which is the corrected amount of the scattered light at the fourth light amount measurements according to the expressions:

$$\text{Slatex3} = Is3/((It2/It1)^{\wedge}(V2/V3)), \text{ and}$$

$$\text{Slatex4} = Is4/((It2/It1)^{\wedge}(V2/V3)),$$

where
It1 is the measured amount of transmitted light at the first light amount measurement,
It2 is the measured amount of transmitted light at the second light amount measurement,
V2 is the liquid amount at the second light amount measurement,
V3 is the liquid amount at the third light amount measurement,
Is3 is the measured amount of scattered light at the third light amount measurement, and
Is4 is the measured amount of scattered light at the fourth light amount measurement.

3. The automatic analysis device according to claim 1, wherein the analysis unit is further programmed to compute the concentration based on Slatex3 which is the corrected amount of the scattered light at the third light amount measurement and Slatex4 which is the corrected amount of the scattered light at the fourth light amount measurements according to the expressions:

$$\text{Slatex3} = Is3/((It1/It0) \times (It2/It1)^{\wedge}(V2/V3)), \text{ and}$$

$$\text{Slatex4} = Is4/((It1/It0) \times (It2/It1)^{\wedge}(V2/V3)),$$

where
It0 is the measured amount of transmitted light at the first light amount measurement under a condition such that a disturbance factor can be disregarded with water dispensed into the reaction cell,
It1 is the measured amount of transmitted light at the first light amount measurement,
It2 is the measured amount of transmitted light at the second light amount measurement,
V2 is the liquid amount at the second light amount measurement,
V3 is the liquid amount at the third light amount measurement,
Is3 is the measured amount of scattered light at the third light amount measurement, and
Is4 is the measured amount of scattered light at the fourth light amount measurement.

4. The automatic analysis device according to claim 1, wherein the analysis unit is further programmed to compute the concentration based on Slatex3 which is the corrected amount of the scattered light at the third light amount measurement and Slatex4 which is the corrected amount of the scattered light at the fourth light amount measurements according to the expressions:

$$\text{Slatex3} = (Is3 - Is2 \times (V2/V3) \times It3/It2)/((It2/It1)^{\wedge}(V2/V3)), \text{ and}$$

$$\text{Slatex4} = (Is4 - Is2 \times (V2/V3) \times It4/It2)/((It2/It1)^{\wedge}(V2/V3)),$$

where
It1 is the measured amount of transmitted light at the first light amount measurement,
It2 is the measured amount of transmitted light at the second light amount measurement,
It3 is the measured amount of transmitted light at the third light amount measurement,
V2 is the liquid amount at the second light amount measurement,
V3 is the liquid amount at the third light amount measurement,
Is2 is the measured amount of scattered light at the second light amount measurement,
Is3 is the measured amount of scattered light at the third light amount measurement, and
Is4 is the measured amount of scattered light at the fourth light amount measurement.

5. The automatic analysis device according to claim 1, wherein the analysis unit is further programmed to display a user interface screen having a check box for inputting an instruction to correct an influence of the sample and/or an influence of the reaction cell.

6. The automatic analysis device according to claim 1, wherein the analysis unit is further programmed to display, in a measurement result display screen, that an influence corrected for by the computation of the concentration is an influence of the sample and/or an influence of the reaction cell.

* * * * *